(12) United States Patent
Kim et al.

(10) Patent No.: US 7,442,714 B2
(45) Date of Patent: Oct. 28, 2008

(54) AMLODIPINE GENTISATE AND A METHOD OF ITS PREPARATION

(75) Inventors: Jae-Sun Kim, Suwon-si (KR); Jin Young Choi, Suwon-si (KR); Je Ho Ryu, Seoul (KR); Nam Kyu Lee, Suwon-si (KR); Jeong-soo Jang, Seongnam-si (KR); Woo Jae Jang, Gunpo-si (KR); Key An Um, Suwon-si (KR); Do Seung Kum, Seoul (KR)

(73) Assignee: SK Chemicals Co., Ltd., Kyungki-Do (KR)

( * ) Notice: Subject to any disclaimer, the term of this patent is extended or adjusted under 35 U.S.C. 154(b) by 0 days.

(21) Appl. No.: 10/583,438

(22) PCT Filed: Dec. 15, 2004

(86) PCT No.: PCT/KR2004/003309

§ 371 (c)(1),
(2), (4) Date: Feb. 8, 2007

(87) PCT Pub. No.: WO2005/058825

PCT Pub. Date: Jun. 30, 2005

(65) Prior Publication Data

US 2007/0135495 A1   Jun. 14, 2007

(30) Foreign Application Priority Data

Dec. 16, 2003   (KR) .................. 10-2003-0092001

(51) Int. Cl.
*A61K 31/44* (2006.01)
*C07D 213/80* (2006.01)

(52) U.S. Cl. ...................... 514/356; 546/321
(58) Field of Classification Search ............... 546/235, 546/321; 514/330, 356
See application file for complete search history.

(56) References Cited

FOREIGN PATENT DOCUMENTS

| EP | 0 089 167 B | 10/1986 |
|---|---|---|
| EP | 0089167 | * 10/1986 |
| EP | 0 244 944 B | 1/1990 |
| KR | 19950007228 | 7/1995 |
| KR | 2004100696 | 12/2004 |
| WO | WO 02/079158 A | 10/2002 |
| WO | WO 03/089414 A | 10/2003 |

OTHER PUBLICATIONS

See Hcaplus 136:334518.*

* cited by examiner

*Primary Examiner*—Janet L. Andres
*Assistant Examiner*—Binta Robinson
(74) *Attorney, Agent, or Firm*—Frommer Lawrence & Haug LLP; Ronald R. Santucci

(57) ABSTRACT

The present invention relates to an acid salt of amlodipine gentisate and a method of its preparation. More particularly, the present invention relates to a crystalline acid salt of amlodipine gentisate of the following formula 1 prepared by reacting amlodipine and gentisic acid, which is useful for the treatment of cardiovascular diseases and has the advantages of low toxicity, excellent stability, improved pharmaceutical efficacies and long-lasting concentration in blood.

5 Claims, 1 Drawing Sheet

AMLODIPINE GENTISATE AND A METHOD OF ITS PREPARATION

This application is a 371 of PCT/KR2004/003309 filed on Dec. 15, 2004, published on Jun. 30, 2005 under publication number WO 2005/058825 A1 which claims priority benefits from Korean Patent Application No. 10-2003-0092001 filed Dec. 16, 2003.

TECHNICAL FIELD OF THE INVENTION

The present invention relates to an acid salt of amlodipine gentisate and a method of its preparation. More particularly, the present invention relates to a crystalline acid salt of amlodipine gentisate of the following formula 1 which is useful for the treatment of cardiovascular diseases. Amlodipine gentisate is prepared by reacting amlodipine and gentisic acid, which has the advantages of low toxicity, excellent stability, improved pharmaceutical efficacies and long-lasting concentration in blood.

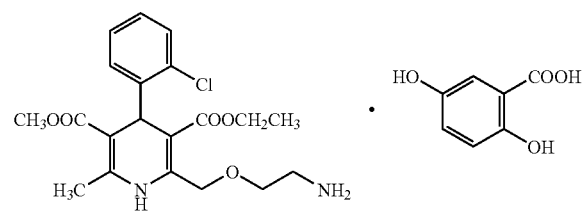

(1)

BACKGROUND OF THE INVENTION

Amlodipine is 3-ethyl-5-methyl-2-(2-aminoethoxy-methyl)-4-(2-chlorophenyl)-6-methyl-1,4-dihydro-3,5-pyridine dicarboxylate and has been used in the treatment of ischemic and hypertensive heart diseases as a calcium-channel blocker. Furthermore, it has been well known that amlodipine is an effective and useful agent due to its prolonged activity.

Amlodipine was first disclosed as a novel compound of 1,4-dihydropyridines in EP Patent Publication No. 89,167. This patent teaches that pharmaceutically acceptable salts of amlodipine can be produced from non-toxic acids with pharmaceutically acceptable anions such as chloride, bromide, sulfate, phophate, acetate, maleate, fumarate, lactate, tartrate, citrate, gluconate, and more preferably maleate.

Free form of amlodipine is also pharmaceutically useful, but it has been administered in the salt form of a pharmaceutically acceptable acid due to its low stability.

Korean Patent No. 90,479 discloses four physicochemical properties, which are required to form pharmaceutically acceptable salts: (1) excellent aqueous solubility; (2) excellent stability; (3) non-hygroscopicity; and (4) processability for tablet formulation. It is, however, very difficult to meet all the four physicochemical property requirements above, and even the maleate salt, which is currently the most preferable pharmaceutical form, has been reported to decompose in the solution within several weeks.

Korean Patent No. 91,020 discloses that amlodipine besylate is superior over conventional salts of amlodipine and has excellent processability for pharmaceutical formulation. However, it has been brought for safety issues since benzenesulfonic acid, which is corrosive and toxic, is used in the process for producing amlodipine besylate.

SUMMARY OF THE INVENTION

The inventors of the present invention have made intensive and thorough researches to overcome the above problems and finally succeeded in preparing a novel crystalline acid salt of amlodipine gentisate by reacting amlodipine with gentisic acid, a relatively less toxic organic acid compared to benzenesulfonic acid. Amlodipine gentisate has low toxicity, superior stability under various conditions such as temperature changes and the presence of water and light as well as superior pharmaceutical effects with a prolonged activity, thereby satisfying all the requirements as a pharmaceutically acceptable salt.

Therefore, an object of the present invention is to provide a pharmaceutically acceptable acid salt of amlodipine with excellent physicochemical properties with low toxicity.

Another object of the present invention is to provide a method for preparing an acid salt of amlodipine gentisate satisfying all the physicochemical property requirements as a therapeutically acceptable salt.

A further object of the present invention is to provide a pharmaceutical composition containing an acid salt of amlodipine gentisate as a therapeutically active ingredient effective in the treatment of cardiovascular diseases.

DETAILED DESCRIPTION OF THE EMBODIMENTS

The present invention relates to an acid salt of amlodipine gentisate of the following formula 1 useful for the treatment of cardiovascular diseases which has the advantages of low toxicity, excellent stability, improved pharmaceutical efficacies and long-lasting concentration in blood.

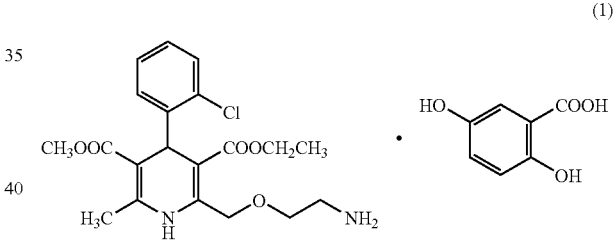

(1)

The acid salt of amlodipine gentisate of the following formula 1 of the present invention includes all the isomers of amlodipine and mixtures thereof.

In another aspect, the present invention relates to a method for preparing a salt of amlodipine gentisate of the above formula 1. The salt of amlodipine gentisate is prepared by reacting amlodipine of the following formula 2 with gentisic acid of the following formula 3 as shown in reaction scheme 1 below.

[Scheme 1]

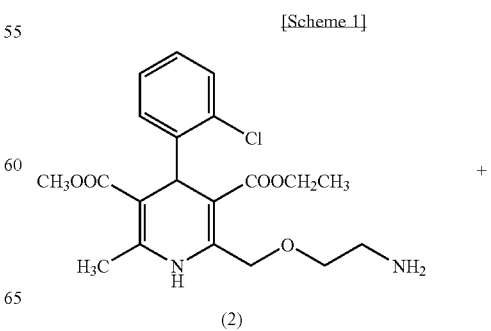

(2)

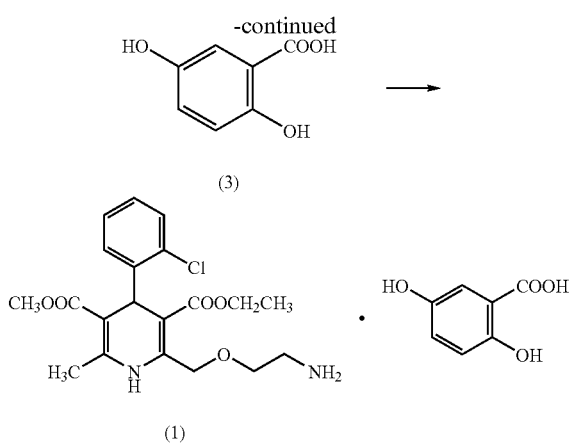

The above reaction scheme 1 for preparing an acid salt of amlodipine comprises the following steps of:
(1) dissolving or suspending amlodipine;
(2) dissolving gentisic acid and adding it to the above amlodipine solution to prepare a mixture; and
(3) stirring the above reaction mixture, and then filtering, washing, and drying resulting solids to produce a crystalline acid salt of amlodipine gentisate.

As stated above, the crystalline acid salt of amlodipine gentisate of the present invention is prepared by adding gentisic acid into the solution containing the amlodipine of the above formula 2. The specific details are shown below.

In step 1, the concentration of amlodipine in the reaction solution is important to effectively accelerate crystallization and preferable to be in the range from about 3 wt % to about 60 wt %. Each isomer of R-amlodipine or S-amlodipine or a mixture of these isomers can be used, more preferably S-amlodipine for efficient pharmaceutical activity.

In step 2, it is preferable to use appropriate amount of gentisic acid in the range from about 0.1 to about 5.0 equivalents over amlodipine. In the steps 1 & 2, water or any conventional organic solvent can be used as a reaction solvent. More preferably, the reaction solvent can be one or a mixture selected from the group consisting of water, methanol, ethanol, isopropannol and acetonitrile.

In step 3, the reaction to form a crystalline acid salt of amlodipine gentisate is performed at a temperature ranging from about −10 to about 60° C.

The amlodipine gentisate is known to have relatively low toxicity compared to that of amlodipine besylate and meet all the physicochemical properties required for pharmaceutically acceptable salt (Experimental Examples 1 & 2). Therefore, the present invention includes a pharmaceutical composition, which contains an isomer or a mixture of isomers of amlodipine gentisate of the above formula 1 as an active ingredient for the treatment of cardiovascular diseases.

The pharmaceutical composition of the present invention may be formulated into oral or parenteral dosage forms or into general pharmaceutically acceptable dosage forms. In the formulation into oral or parenteral dosage forms, a pharmaceutically acceptable filler, a diluent, a binder, a wetting agent, a disintegrant, a surfactant or an excipient may be combined. Examples of solid dosage forms for the oral administration include tablets, granules, powders, capsules and the like. Such solid dosages may contain at least one excipient such as starch, sucrose, lactose and gelatin. Additionally, lubricating agent such as magnesium stearate and talc may be included.

Examples of liquid preparation for the oral administration include suspensions, solutions, emulsions, syrups and the like, and such liquid forms may contain diluent such as water and aqueous paraffin, and excipient such as a wetting agent, a sweetening agent, a flavoring agent, a preserving agent and the like. Examples of the formulation for the parenteral administration include sterile aqueous solution, non-aqueous solution, suspensions, emulsions, lyophillized preparation, and suppositories. Injectable ester such as ethyl olate and vegetable oil such as propylene glycol, polyethylene glycol and olive oil may be used for non-aqueous solution and suspensions. The suppository preparation can be prepared by using a base such as witepsol, macrogol, Tween 61, cacao oil, laurin oil, glycerol-gelatin and the like.

The amount of the pharmaceutical composition actually administered will be determined in the light of the relevant circumstances, including the patient's age, weight, and sex, the selected route of administration, the condition to be treated, the severity of the patient's symptoms, and the like. According to physician or pharmacist, a compound can be administered in a single daily dose or in multiple doses per day. Suitable doses of the amlodipine gentisate are 1.0-10.0 mg per day based on the amlodipine base.

EXAMPLE

Figure 1:
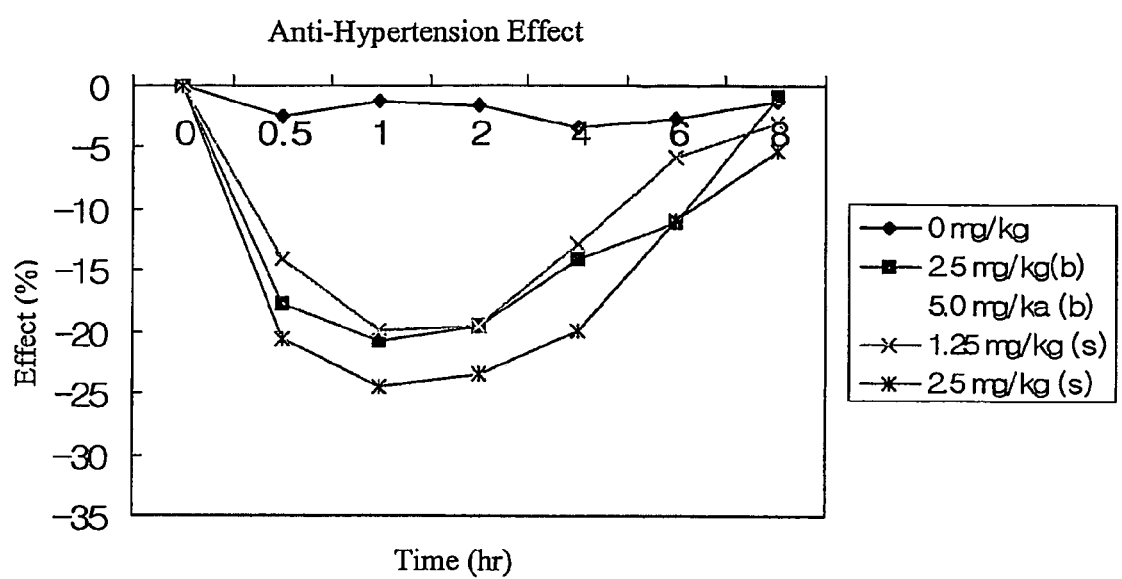
FIG. 1 is showing the antihypertensive effect of (±)-amlodipine besylate salt or S-(−)-amlodipine gentisate.

A better understanding of the present invention may be obtained in light of the following examples which are set forth to illustrate, but are not to be construed to limit the present invention.

Example 1

Preparation of (R,S)-(±)-Amlodipine Gentisate Salt 5 g (12.2 mmol) of (R,S)-(±)-amlodipine gentisate salt was dissolved in 30 mL of ethanol and the mixture was cooled down to 5° C. Then, 1.88 g (12.2 mmol) of gentisic acid was dissolved in 20 mL of ethanol and slowly added to the above amlodipine solution. The reaction solution was stirred at room temperature for 2 hr. After washing with 20 mL of cold water, the solid produced thereof was filtered out and vacuum-dried at 50° C. to obtain 6.62 g of the desired bright yellow crystalline compound (yield 96.2%).

m.p. 156-159° C.; $^1$H-NMR(300 MHz, DMSO-d6) δ(ppm) 7.35-7.12(m, 5H, ArH), 6.61(d.d., 1H), 6.47(d, 1H), 5.31(s, 1H), 4.74-4.55(d.d., 2H), 3.99-3.94(m, 2H), 3.68(brt, 2H), 3.50(s, 3H), 3.09(brt, 2H), 2.30(s, 3H), 1.10(t, 3H)

Example 2

Preparation of (S)-(−)-Amlodipine Gentisate Salt 5 grams (12.2 mmol) of (S)-(−)-amlodipine gentisate salt was suspended in 7.5 mL of ethanol and stirred. Then, 1.9 g (12.3 mmol) of gentisic acid was dissolved in 50 mL of water and slowly added to the above amlodipine solution. The reaction solution was stirred at room temperature for 2 hr. After washing with 20 mL of cold water, the solid produced thereof was filtered out and vacuum-dried at 50° C. to obtain 6.61 g of the desired bright yellow crystalline compound (yield 96%).

m.p. 162-165° C.; $^1$H-NMR(300 MHz, DMSO-d6) δ(ppm) 7.35-7.11(m, 5H, ArH), 6.62(d.d., 1H), 6.48(d, 1H), 5.30(s, 1H), 4.74-4.55(d.d., 2H), 3.99~3.95(m, 2H), 3.68(brt, 2H), 3.50(s, 3H), 3.10(brt, 2H), 2.30(s, 3H), 1.10(t, 3H); empirical values of elementary analysis for $C_6H_{31}N_2O_9Cl$: C, 57.40%; H, 5.60%; N, 4.80% Calculated Value: C, 57.60%; H, 5.55%; N, 4.98%; Chiral HPLC: 99.9% e.e.

Example 3

Formulation of Tablets Containing Amlodipine Gentisate Salt 315 g of anhydrous calcium hydrogen phosphate and 525 g of microcrystalline cellulose (90 μm) were mixed and then transferred to a drum. Then, 70 g of amlodipine gentisate salt and 187.5 g of microcrystalline cellulose (50 μm) were mixed and then passed through a screen into the above drum. The above screen was washed with 525 g of microcellulose (90 μm). After adding 315 g of anhydrous calcium hydrogen phosphate to the above mixture, the entire mixture was blended for 10 min and then added with 40 g of sodium starch glycolate and then blended again for another 6 min. Finally, 20 g of magnesium stearate was added and the resulting product was blended for 3 min and the powder mixture was compressed via a conventional method to form a tablet.

Example 4

Formulation of Capsules Containing Amlodipine Gentisate Salt 525 g of microcrystalline cellulose (90 μm) and dry corn starch was premixed. 70 g of amlodipine gentisate salt was mixed with a part of the above premixture and then sieved out. The remaining premixture was mixed for 10 min, sieved and then mixed for another 5 min. Finally, the resulting mixture was filled into capsules with appropriate size for capsule preparation.

Example 5

Formulation of Injections Containing Amlodipine Gentisate Salt

Sodium chloride was dissolved in sterile water for injection and mixed with propylene glycol. The mixture was then added with amlodipine gentisate salt to be dissolved and then added with sterile water to adjust the solution to a desired concentration. Finally, the solution was filtered out through a sterile filter and then filled into sterile ampoules for injection preparation.

Experimental Example 1

Test for Oral Toxicity

Oral toxicities of benzenesulfonice acid, which forms the crystalline acid salt of amlodipine besylate, and gentisic acid, which forms the crystalline acid salt of amlodipine gentisate, are compared in the following table 1. The data for benzenesulfonic acid was retrieved from the Registry of Toxic Effects of Chemical Substances (RTECS).

TABLE 1

| Acid | Administration | Tested animal | Dosage | Reference |
|---|---|---|---|---|
| Benzenesulfonic acid | oral | rat | $LD_{50}$ 890 μl/kg | AIHAAP 23, 95, 1962 |
| | oral | wild bird | $LD_{50}$ 75 mg/kg | TXAPA9 21, 315, 1972 |
| Gentisic acid | oral | mouse | $LD_{50}$ 4,500 mg/kg | BJPCAL 8, 30, 1953 |
| | abdominal | rat | $LD_{50}$ 3,000 mg/kg | BCFAAI 112, 53, 1973 |

$LD_{50}$: 50% Lethal Dose

As shown in Table 1, it is noted that benzenesulfonic acid itself, which has been generally used for preparing crystalline acid salt of amlodipine, shows somewhat higher toxicity, while the gentisic acid used for preparing crystalline acid salt of amlodipine in the present invention shows relatively lower toxicities compared to that of benzenesulfonic acid.

Experimental Example 2

Test for Stability

This experiment is designed to confirm the stability of amlodipine salt. It is essential for a drug to have sufficient stability in order to be formulated into a specific form of preparation. In particular, it is especially important to have an atmospheric stability for a drug to be formulated into tablets or capsules while aqueous stability is more important when a drug is formulated into an injection type of preparation.

The following table 2 shows the results of HPLC analysis monitoring the contents of the active ingredients with reference to their initial values after storing (±)-amlodipine besylate and S-(−)amlodipine gentisate, respectively, at 40° C. with 75% humidity for a period of 2, 4 and 8 weeks. The following table 3 shows the results of the same at a different condition of 60° C. with 75% humidity.

TABLE 2

| Content of active ingredients at 40° C. with 75% humidity (%) | | | | |
|---|---|---|---|---|
| amlodipine salt | initial | 2 weeks | 4 weeks | 8 weeks |
| (±)-amlodipine besylate | 100 | 99.9 | 99.8 | 99.2 |
| S-(−)-amlodipine besylate | 100 | 101.1 | 101.7 | 101.6 |
| S-(−)-amlodipine gentisate | 100 | 102.9 | 103.5 | 102.3 |

TABLE 3

| Content of active ingredients at 60° C. with 75% humidity (%) | | | | |
|---|---|---|---|---|
| amlodipine salt | initial | 2 weeks | 4 weeks | 8 weeks |
| (±)-amlodipine besylate | 100 | 98.7 | 97.4 | 98.1 |
| S-(−)-amlodipine besylate | 100 | 100.1 | 98.5 | 96.3 |
| S-(−)-amlodipine gentisate | 100 | 100.1 | 103.0 | 99.9 |

Table 4 represents the result of light stability of amlodipine gentisate salts of the present invention compared to that of amlodipine besylate and the total amount of UV light was 200 W·h/m².

TABLE 4

| | Content of active ingredients (%) | |
|---|---|---|
| amlodipine salt | Initial | UV |
| (±)-amlodipine besylate | 100 | 88.3 |
| S-(−)-amlodipine besylate | 100 | 90.1 |
| S-(−)-amlodipine gentisate | 100 | 100.7 |

As shown in tables 2-4, S-(−)-amlodipine gentisate salt superior light stability under UV or visible light as compared to that of conventional amlodipine besylate salts.

Experimental Example 3

Test of Concentration of Active Ingredients in Blood After Oral Administration Sprague Dowry rats having body weights of 250-270 g were orally administered with S-(1)-amlodipine gentisate and (±)-amlodipine besylate 10 mg/kg (free base), and blood samples were collected from them using a heparin-treated pipet at 0.5, 1, 2, 4, 6 and 8 hr after the administration. The blood samples were centrifuged for 2 min at 14,000 rpm to obtain blood plasma. 80 μL of the blood plasma was mixed with 240 μL of methanol and vortexed for 10 sec and centrifuged again for 2 min at 14,000 rpm. The supernatant was stored at −80° C. until it was analyzed, and mobile phase (35% acetonitrile/20 mM $KH_2PO_4$) was flowed onto the reverse-phase C-18 Capcell-pak column, which is connected to C-18 guard column) at the rate of 1.0 mL/min.

The following Table 5 shows the concentration of the active material (amlodipine) collected from blood according to time passage.

TABLE 5

| Time after administration (hr) | Blood Concentration of active material after administration (g/mL) | |
|---|---|---|
| | S-(−)-amlodipine gentisate | (±)-amlodipine besylate |
| 0.5 | 0.083 ± 0.01 | 0.089 ± 0.04 |
| 1 | 0.165 ± 0.02 | 0.149 ± 0.04 |
| 2 | 0.205 ± 0.02 | 0.198 ± 0.04 |
| 4 | 0.245 ± 0.02 | 0.215 ± 0.05 |
| 6 | 0.259 ± 0.01 | 0.192 ± 0.02 |
| 8 | 0.220 ± 0.01 | 0.166 ± 0.01 |

Each of the above values indicates mean standard deviation (n = 5).

As shown in Table 5, S-(−)-amlodipine gentisate showed the highest concentration in blood after administration in rats during the physiologically useful period of 4-6 hr after the administration, and the value was higher than that of (±)-amlodipine besylate by about 120%.

Experimental Example 4

Comparison of Pharmaceutical Efficacies Between Optically Active S-(−)-Amlodipine Gentisate and (±)-Amlodipine Besylate This experiment is designed to compare the anti-hpertension activities between the salts of S-(−)-amlodipine gentisate and (±)-amlodipine besylate. Rats with congenital hypertension (SHR, male, 13-14 weeks old) were purchased from Charles River Co. (Japan). The rats were allowed to remain stable in a clean test animal breeding chamber, which is kept at constant temperature of 22.5±1° C. and humidity of 55±5% under automatic illumination control every 12 hours, and then placed to the experiment thereafter. SHR were used those having systolic blood pressure of 170 mmHg or higher and each experimental group was composed of 8 rats. Blood pressure was measured using Multichannel 8000 (TSE Co., Germany) according to the tail-cuff method. For easy measurements, the rats were confined in a container kept at 37° C. for 10 min and administered orally with 5 mg/kg of a test substance after dissolving it in distilled water (1.0 mL/100 g rat). Measurements of blood pressure were made in 2, 4, 6, 8, 10 and 24 hr after the administration, respectively. The result of measurements was indicated in S.E.M. Statistical analysis of the measurements was performed by using Sigma Stat program (Jandel Co., USA) with respect to unpaired t-test and one-way analysis of variance (ANOVA) and the second evaluation was performed via Dunnett multiple comparisons test. The results of the anti-hpertension activities of the salts of S-(−)-amlodipine gentisate and (±)-amlodipine besylate on the rats with congenital hypertension are shown in FIG. 1, Tables 6 and 7.

TABLE 6

Anti-hpertension activity of the salts of (±)-amlodipine besylate

| Administration (mg/kg) | Decrease in Blood Pressure (%) |
|---|---|
| 2.5 | 20.8 ± 7.3 |
| 5.0 | 28.6 ± 7.5 |

TABLE 7

Anti-hpertension activity of the salts of S-(−)-amlodipine gentisate

| Administration (mg/kg) | Decrease in Blood Pressure (%) |
|---|---|
| 1.25 | 19.8 ± 5.5 |
| 2.5 | 24.5 ± 7.9 |

In both groups of rats administered orally with the salts of (±)-amlodipine besylate (Table 6) and S-(−)-amlodipine gentisate (Table 7) exhibited dosage-dependent anti-hypertension effect, and the trends in decrease in blood pressure were also shown very similar in all experimental groups. Both test substances started to show a significant level of decrease in blood pressure 30 min after the administration and the level of decrease reached the peak 1 hr after the administration. The anti-hypertension effect was shown significant until 6 hr after the administration. In particular, the salts of optically active S-(−)-amlodipine gentisate showed a similar level of anti-hypertension effect that of the salts of (±)-amlodipine besylate when used only in half dose. That is, the maximum anti-hypertension effect of the salts of (±)-amlodipine besylate were 20.8±7.3% at the dosage of 2.5 mg/kg, while the maximum anti-hypertension effect of the salts of optically active S-(−)-amlodipine gentisate was 19.8±5.5% at the dosage of 1.25 mg/kg, which is only half of that of the the salts of (±)-amlodipine besylate. Furthermore, at the dosage of 5 mg/kg, the maximum anti-hypertension effect of the salts of (±)-amlodipine besylate were 28.6±7.5%, while the maximum anti-hypertension effect of the salts of optically active S-(−)-amlodipine gentisate was 24.5±7.9% at the dosage of 2.5 mg/kg.

Therefore, it was shown that both the salts of (±)-amlodipine besylate and S-(−)-amlodipine gentisate exhibit dosage-dependent anti-hypertension effect. Furthermore, from the result that the salts of optically active S-(−)-amlodipine gentisate can show similar level of anti-hypertension effect by using half the amount of the salts of (±)-amlodipine besylate, it can be concluded that the anti-hypertension effect of the salts of optically active S-(−)-amlodipine gentisate is twice superior to that of the salts of (±)-amlodipine besylate.

As stated above, the amlodipine gentisate of the present invention is a crystalline acid salt of amlodipine suitable for pharmaceutical preparations while it uses a less toxic substance of gentisic acid unlike the typical salts of amlodipine besylate with a highly toxic substance of benzenesulfonic acid and still satisfys all the physicochemical requirements which are at least equivalent to those of amlodipine besylate, thereby being useful as a pharmaceutical composition for the treatment of cardiovascular diseases.

The invention has been described in detail with reference to preferred embodiments thereof. However, it will be appreciated that those skilled in the art, upon consideration of the disclosure, may make modifications and improvements within the scope and spirit of the invention.

What is claimed is:

1. An (S)-(−)-amlodipine gentisate of the following formula 1

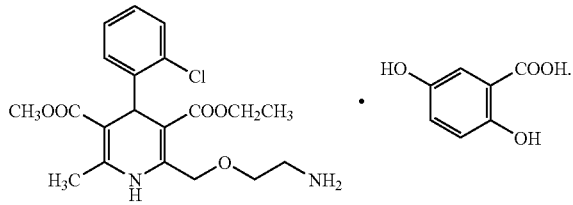

2. A composition comprising the the amlodipine gentisate of the formula 1 in a pharmaceutically acceptable carrier.

3. The composition of claim 2, wherein said pharmaceutical composition is prepared in the form of tablets, capsules or injections.

4. A method of treating hypertension, which comprises administering a therapeutically effective amount of (S)-(−)-amlodipine gentisate of claim 1.

5. A method of treating hypertension, which comprises administering a therapeutically effective amount of (S)-(−)-amlodipine gentisate of claim 2.

* * * * *